United States Patent [19]

Someya et al.

[11] Patent Number: 4,608,081

[45] Date of Patent: Aug. 26, 1986

[54] HERBICIDAL 2-[4-(4-CYANOPHENOXY)-PHENOXY]-ALKANOIC ACID AMIDES

[75] Inventors: Shinzo Someya, Tokorozawa; Rokuro Akahira, Kurume; Yuji Nonaka, Tokuyama; Akira Nakanishi, Shinnanyo; Mikio Ito, Tokuyama, all of Japan

[73] Assignees: Kanesho Company Limited, Tokyo; Toyo Soda Manufacturing Company Limited, Shinnanyo, both of Japan

[21] Appl. No.: 623,519

[22] Filed: Jun. 22, 1984

[51] Int. Cl.$^4$ .................... A01N 43/40; A01N 37/34; C07D 213/74; C07C 121/52

[52] U.S. Cl. .................................. 71/94; 71/105; 71/103; 546/292; 546/308; 546/309; 546/287; 260/397.6; 558/413; 558/414

[58] Field of Search ............... 546/309, 287, 308, 292; 260/397.6, 465 D; 71/94, 105, 103

[56] References Cited

U.S. PATENT DOCUMENTS

| | | | |
|---|---|---|---|
| 3,515,744 | 6/1970 | Steinbrunn et al. | 546/309 |
| 4,254,262 | 3/1981 | Koike et al. | 546/287 |
| 4,332,961 | 6/1982 | Takahashi et al. | 546/309 |
| 4,443,248 | 4/1984 | Hokama | 260/465 D |

FOREIGN PATENT DOCUMENTS 53-9740  1/1978  Japan.
55-62043  5/1980  Japan.

Primary Examiner—Henry R. Jiles
Assistant Examiner—Dale A. Bjorkman
Attorney, Agent, or Firm—Oblon, Fisher, Spivak, McClelland & Maier

[57] ABSTRACT

Novel compounds in the form of 2-[4-(4-cyanophenoxy)-phenoxy]-propionic or acetic acid amide derivatives and selective herbicides containing the same as an active ingredient.

27 Claims, No Drawings

HERBICIDAL 2-[4-(4-CYANOPHENOXY)-PHENOXY]-ALKANOIC ACID AMIDES

DETAILED DESCRIPTION OF THE INVENTION

This invention concerns novel compounds and selective herbicides containing said compounds.

More specifically, this invention concerns 2-[4-(4-cyanophenoxy)-phenoxy]-alkanoic acid amide derivatives represented by a following general formula (I)

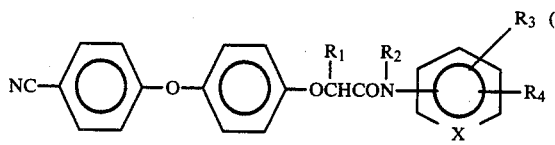

wherein $R_1$ denotes hydrogen atom or methyl group, $R_2$ denotes hydrogen atom or lower alkyl group, $R_3$ denotes hydrogen atom, halogen atom, lower alkyl group, lower alkoxy group, cyano group, nitro group, trifluoromethyl group, lower alkylaminocarbonyl group or lower alkanesulfonyloxy group, $R_4$ denotes hydrogen atom, halogen atom or lower alkyl group, X denotes methine group or nitrogen atom and herbicides characterized in containing said compound of this invention as an active ingredient.

The object of this invention lies in providing said compounds industrially and supplying effective and selective herbicides containing said compounds as an active ingredient.

The compounds of this invention display an extremely excellent herbicidal activity against barnyard grass, which is one of the most harmful weeds, especially by applications to water-surface of a paddy field in the paddy field rice cultivation. In addition, said compounds are substantially harmless against rice plants in every stage from direct seeding to transplanting, and hence they show a herbicidal activity which is selective between species of plants. Hitherto, herbicidal treatments of barnyard grass which is main weed of the paddy field have been carried out by a method of depressing only barnyard grass in the stage of germination without giving any harm to growth-advanced rice plant with utilizing differences between their durability against applied drug due to differences of growth stages between barnyard grass and rice plant, or a physical selection method of hampering germination of barnyard grass seed positioned in drug-absorbing layers without giving damage to rice plant distributed outside the drug-absorbing layers. Accordingly, these herbicides have been extremely difficult to be applied to flooded field for directly seeded rice plants or young seeding of rice plants immediately after transplanted.

Upon reviewing compounds having physiologically selective activity inherent in the drug between rice plant and barnyard grass in order to provide herbicides which are safely applicable to weak rice plant such as seeded rice plant, the inventors of this invention have found that the compound of this invention has a remarkable selectivity between species, does not give any substantial damage to rice plant, shows a strong herbicidal activity against barnyard grass, maintains this activity for extremely long period, shows also small value in variation of the activity due to kind of soil, and hence it can be applicable in a broad scope from flooded seeded rice plant and transplanted rice plant.

The compound of this invention does not give any substantial harm to broad leaved crops such as radishes, peas, spinaches, soybean, azuki bean, beat, cotton and the like, in foliage treatment thereof, even in such a drug amount capable to kill completely, for example, Setaria species, Echinochloa, Digitaria species, Rottboellia species and Avenafatua species. Moreover, it does not cause any effect on broad leaved crops and grains such as rice plant, barley plant and wheat plant, in soil treatment before germination of weeds, even in such a drug amount capable to inhibit completely germination of barnyard grass, crab grass, foxtail and so forth. Therefore, the compounds of this invention was proved to show an extremely broad scope of applicability.

The compounds of this invention can be prepared according to the following reaction equations (1) and (2), wherein Hal denotes a halogen atom, and $R_1$, $R_2$, $R_3$, $R_4$ and X have the same meanings as above-mentioned respectively in the following reaction equations.

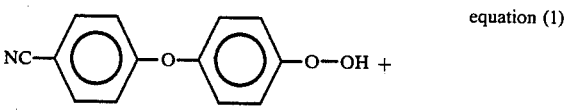

equation (1)

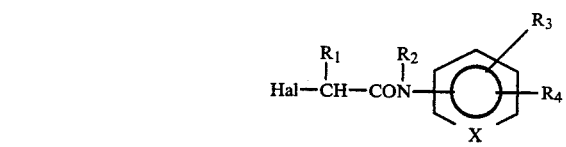

the general formula (I) + H.Hal

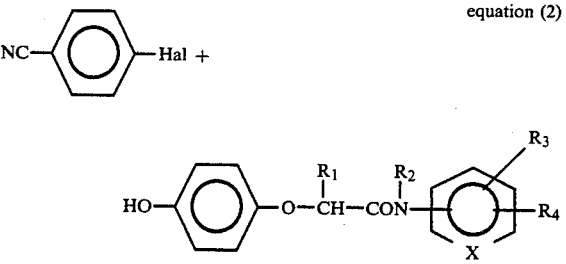

equation (2)

the general formula (I) + H.Hal

The above reactions can be performed in the presence of a reaction solvent and a base.

As the reaction solvent, water ketones such as acetone, methylethylketone and the like, aromatic hydrocarbons such as benzene, toluene, xylene and the like, ethers such as ethylether, tetrahydrofuran, dioxane and the like, alcohols such as methanol, ethanol, isopropanol, butanol and the like, halogenated hydrocarbons such as chlorobenzene, chloroform, carbon tetrachloride, dichloroethane and the like, dimethylformamide, dimethylsulfoxide, and so on can be employed.

As the base, for example, alkali hydroxides such as sodium hydroxide, potassium hydroxide and the like, alkali carbonates such as sodium carbonate, potassium carbonate, sodium bicarbonate and the like, alcohlates such as sodium ethoxide and the like, tertiary amines such as triethylamine, dimethylaniline, pyridine and the like can be employed. The reaction temperature is between 0° C. and 200° C. and the reaction period is within one hour to several days, but the reaction period depends on the selected solvent and reaction temperature.

Moreover, the compound of this invention can be prepared according to the following reaction equations, wherein Hal denotes a halogen atom and $R_1$, $R_2$, $R_3$, $R_4$ and X have the same meanings as above-mentioned in the following reaction equations.

equation (3)

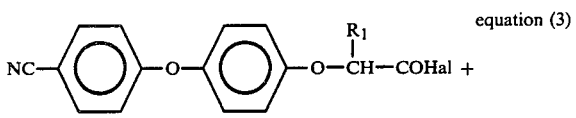

the general formula (I) + H.Hal equation (4)

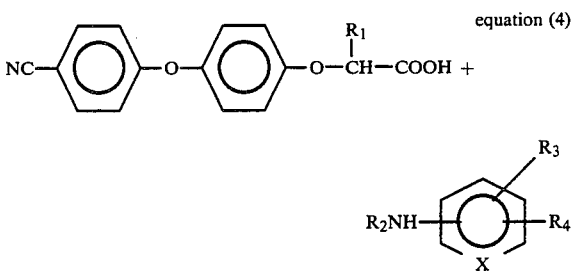

the general formula (I) + H$_2$O

The reaction of equation (3) can be carried out in the presence or absence of a reaction solvent and a base. As the reaction solvent, the before said ketones, ethers, hydrocarbons, dimethyformamide, dimethylsulfoxide and the like can be employed. As the base, the before said can be used. The reaction can proceed usually at a temperature of 0°–150° C. and the reaction period can be several minutes to about 48 hours. The reaction of equation (4) can proceed with heating a mixture of carboxylic acid and aniline at a high temperature or with removal of resulting water through an azeotropic distillation. Moreover, it can proceed rapidly in a mild condition with addition of a condensation agent such as carbodiimides. Representative examples of the compounds of this invention and their properties are shown below.

| No. | Example of the compounds of this invention and their properties |
|---|---|
| 1. | N—Phenyl-2-[4-(4-cyanophenoxy)-phenoxy]-propionamide, m.p. 133–134° C. |
| 2. | N—(2-Fluorophenyl)-2-[4-(4-cyanophenoxy)-phenoxy]-propionamide, m.p. 134–135.5° C. |
| 3. | N—(3-Fluorophenyl)-2-[4-(4-cyanophenoxy)-phenoxy]-propionamide, m.p. 102–105° C. |
| 4. | N—(4-Fluorophenyl)-2-[4-(4-cyanophenoxy)-phenoxy]-propionamide, m.p. 118.5–120° C. |
| 5. | N—(2-Chlorophenyl)-2-[4-(4-cyanophenoxy)-phenoxy]-propionamide, m.p. 101.5–103° C. |
| 6. | N—(3-Chlorophenyl)-2-[4-(4-cyanophenoxy)-phenoxy]-propionamide, m.p. 75–79° C. |
| 7. | N—(4-Chlorophenyl)-2-[4-(4-cyanophenoxy)-phenoxy]-propionamide, m.p. 137–139° C. |
| 8. | N—(2-Methoxyphenyl)-2-[4-(4-cyanophenoxy)-phenoxy]-propionamide, $n_D^{25}$ 1.5945 |
| 9. | N—(3-Methoxyphenyl)-2-[-4-(4-cyanophenoxy)-phenoxy]-propionamide, m.p. 118–119.5° C. |
| 10. | N—(4-methoxyphenyl)-2-[4-(4-cyanophenoxy)-phenoxy]-propionamide, m.p. 134–136° C. |
| 11. | N—(2-Methylphenyl)-2-[4-(4-cyanophenoxy)-phenoxy]-propionamide, m.p. 124–125.5° C. |
| 12. | N—(3-Methylphenyl)-2-[4-(4-cyanophenoxy)-phenoxy]-propionamide, m.p. 78–80° C. |
| 13. | N—(4-Methylphenyl)-2-[4-(4-cyanophenoxy)-phenoxy]-propionamide, m.p. 137–137.5° C. |
| 14. | N—(3,5-Dichlorophenyl)-2-[4-(4-cyanophenoxy)-phenoxy]-propionamide, m.p. 115–115.5° C. |
| 15. | N—(4-Chloro-2-fluorophenyl)-2-[4-(4-cyanophenoxy)-phenoxy]-propionamide, m.p. 131.5–133° C. |
| 16. | N—(2-Pyridyl)-2-[4-(4-cyanophenoxy)-phenoxy]-propionamide, $n_D^{25}$ 1.5991 |
| 17. | N—(3-Pyridyl)-2-[4-(4-cyanophenoxy)-phenoxy]-propionamide, viscous oil |
| 18. | N—(4-Pyridyl)-2-[4-(4-cyanophenoxy)-phenoxy]-propionamide, m.p. 52–54° C. |
| 19. | N—(2-Chloro-3-pyridyl)-2-[4-(4-cyanophenoxy)-phenoxy]-propionamide, m.p. 118–119° C. |
| 20. | N—(3,5-Dichloro-2-pyridyl)-2-[4-(4-cyanophenoxy)-phenoxy]-propionamide, m.p. 159–160° C. |
| 21. | N—(3-Methyl-2-pyridyl)-2-[4-(4-cyanophenoxy)-phenoxy]-propionamide, m.p. 62–64° C. |
| 22. | N—(4-Methyl-2-pyridyl)-2-[4-(4-cyanophenoxy)-phenoxy]-propionamide, Viscous oil |
| 23. | N—(6-Methyl-2-pyridyl)-2-[4-(4-cyanophenoxy)-phenoxy]-propionamide, m.p. 109–111° C. |
| 24. | N—Methyl-N—(2-pyridyl)-2-[4-(4-cyanophenoxy)-phenoxy]-propionamide, m.p. 116–118° C. |
| 25. | N—(6-Chloro-2-pyridyl)-N—methyl-2-[4-(4-cyanophenoxy)-phenoxy]-propionamide, m.p. 111–112.5° C. |
| 26. | N—Methyl-N—(5-methyl-2-pyridyl)-2-[4-(4-cyanophenoxy)-phenoxy]-propionamide, m.p. 114–115° C. |
| 27. | N—(2-Chloro-4-pyridyl)-2-[4-(4-cyanophenoxy)-phenoxy]-propionamide, m.p. 138–140° C. |
| 28. | N—(5-Chloro-2-pyridyl)-2-[4-(4-cyanophenoxy)-phenoxy]-propionamide, m.p. 113–115° C. |
| 29. | N—(5-Methyl-2-pyridyl)-2- 8 4-(4-cyanophenoxy)-phenoxy]-propionamide, $n_D^{25}$ 1.5917 |
| 30. | N—(2-Cyanophenyl)-2-[4-(4-cyanophenoxy)-phenoxy]-propionamide, m.p. 114–116° C. |
| 31. | N—(4-Cyanophenyl)-2-[4-(4-cyanophenoxy)-phenoxy]-propionamide, m.p. 140–141° C. |
| 32. | N—(3-Chloro-4-methylphenyl)-2-[4-(4-cyanophenoxy)-phenoxy]-propionamide, m.p. 89–91° C. |
| 33. | N—(3,4-Dimethylphenyl)-2-[4-(4-cyanophenoxy)-phenoxy]-propionamide, m.p. 104–106° C. |
| 34. | N—(4-Ethylphenyl)-2-[4-(4-cyanophenoxy)-phenoxy]-propionamide, m.p. 138–140° C. |
| 35. | N—(4-Propylphenyl)-2-[4-(4-cyanophenoxy)-phenoxy]-propionamide, m.p. 127–130° C. |
| 36. | N—(2-Chloro-5-trifluoromethylphenyl)-2-[4-(4-cyanophenoxy)-phenoxy]-propionamide, m.p. 103–105° C. |
| 37. | N—(3-Chloro-2-methylphenyl)-2-[4-(4-cyanophenoxy)-phenoxy]-propionamide, m.p. 138–140° C. |
| 38. | N—(2-Chloro-4-nitrophenyl)-2-[4-(4-cyanophenoxy)-phenoxy]-propionamide, m.p. 180–182° C. |
| 39. | N—(6-Chloro-2-pyridyl)-2-[4-(4-cyanophenoxy)-phenoxy]-acetamide, m.p. 112–114° C. |
| 40. | N—(6-Chloro-2-pyridyl)-N—methyl-2-[4-(4-cyanophenoxy)-phenoxy]-acetamide, $n_D^{25}$ 1.5996 |
| 41. | N—(3-Butylaminocarbonylphenyl)-2-[4-(4-cyanophenoxy)-phenoxy]-propionamide, m.p. 61–64° C. |
| 42. | N—(3-Methylsulfonyloxyphenyl)-2-[4-(4-cyanophenoxy)-phenoxy]-propionamide, m.p. 140–140.5° C. |
| 43. | N—(6-Chloro-2-pyridyl)-2-[4-(4-cyanophenoxy)-phenoxy]-propionamide, m.p. 140–141.5° C. |
| 44. | N—(3-Isopropoxyphenyl)-2-[4-(4-cyanophenoxy)-phenoxy]-propionamide, $n_D^{25}$ 1.5818 |
| 45. | N—(6-Methoxy-2-pyridyl)-2-[4-(4-cyanophenoxy)-phenoxy]-propionamide, $n_D^{25}$ 1.5739 |
| 46. | N—(4,6-Dimethyl-2-pyridyl)-2-[4-(4-cyanophenoxy)-phenoxy]-propionamide, $n_D^{25}$ 1.5900 |

The compounds of this invention can be used as herbicides in forms of formulations such as emulsifiable concentrates, water dispersible powders, dusts, granules, and the like by admixing, for example, dilution agent, solvent, surface active agent and the like. Therewith, for purpose of lowering labor for scattering or of increasing spectrum of effectively removable weed species, it is sometimes preferable to add other herbicides such as the followings:

2,4-Dichlorophenoxyacetic acid, salts thereof, esters thereof and alkylamine salts thereof.
2-Methyl-4-chlorophenoxyacetic acid, salts thereof and esters thereof.
2-Methyl-4-chlorophenoxybutyric acid, salts thereof and esters thereof.
D,L-2-(4-Chloro-o-tolyloxy)propionic acid, salts thereof and esters thereof.
4-Cyano-2,6-diiodophenyl octanoate.
2,4-Dichlorophenyl-4'-nitrophenylether.
2,4,6-Trichlorophenyl-4'-nitrophenylether.
2,4-Dichlorophenyl-3'-methoxy-4'-nitrophenylether.
3,4-Dichlorocarbanilidic acid methyl.
3-Chlorocarbanilidic acid isopropyl.
Diethylthiocarbamidic acid S-4-chlorobenzyl.
4-Nitrophenyl-3',5'-xylylether.
Hexahydro-1H-azepine-1-carbothionic acid 3,4-dichloropropionanilide.
2-Chloro-2',6'-diethyl-N-(butoxymethyl)acetanilide.
2-Chloro-2',6'-diethyl-N-(m-propoxyethyl)acetanilide.
1-($\alpha,\alpha'$-Dimethylbenzyl)-3-p-tolylurea.
2,4-Bis(ethylamino)-6-methylthio-1,3,5,-triazine.
2-Ethylamino-4-isopropylamino-6-methylthio-1,3,5-triazine.
2,4-Bis(ethylamino)-6-methylthio-1,3,5-triazine.
2-Ethylamino-4-isopropylamino-6-methylthio-1,3,5-triazine.
2,4-Bis(isopropylamino)-6-methylthio-1,3,5-triazine.
5-tert-Butyl-3-(2,4-dichloro-5-isopropoxyphenyl)-1,3,4-oxadiazoline-2-one.
2,6-Dichlorobenzonitril.
2,6-Dichlorothiobenzamide.
2-Amino-3-chloro-1,4-naphthoquinone.
2,4-Dichlorophenyl-3'-carbomethoxy-4'-nitrophenylether.
N-p-Chlorobenzyloxyphenyl-3,4,5,6-tetrahydrophthalimide.
2,4-Dichlorophenyl-3'-ethoxyethoxyethoxy-4'-nitrophenylether.
N-(1-Ethylpropyl)-2,6-dinitro-3,4-xylidine.
4-(2,4-Dichlorobenzoyl)-1,3-dimethyl-pyrazole-5-yl-p-toluenesulfonate.
4-(2,4-Dichlorobenzoyl)-1,3-dimethyl-5-(benzoylmethoxy)-pyrazole.
4-(2,4-Dichloro-3-methylbenzoyl)-1,3-dimethyl-5-(benzoylmethoxy)pyrazole.
O,O-Diisopropyl-2-(benzenesulfonamide)-ethylenedithiophosphate.
3,3'-Dimethyl-4-methoxybenzophenone.
2-(2-Naphthoxy)-propionanilide.
O-Ethyl-O-(3-methyl-6-nitrophenyl)-N-sec-butylphosphorothioamidate.
3-Isopropyl-2,1,3-benzothiadiazinone-(4)-2,2-dioxide and salts thereof.
S-(2-Methyl-1-piperizyl-carbonylmethyl)-O,O-di-n-propyl-dithiophosphate.
S-Benzyl-N,N-dimethylthiocarbamate.

It is possible to provide a mixed herbicide which is active against many weeds species by combining the compound of this invention appropriately with one or more of the above-described herbicides. Next, this invention is explained by employing example, but this invention is not restricted to these examples.

SYNTHESIS EXAMPLE 1

N-Phenyl-2[4-(4-cyanophenoxy)-phenoxy]-propionamide(Compound No. 1)

To 30 ml of acetone were added 1.06 g of 4-(4-cyanophenoxy)-phenol, 0.99 g of $\alpha$-bromopropionanilide and 0.83 g of anhydrous potassium carbonate, and the mixture wask subjected to reflux for 16 hours with stirring. After the reaction mixture was cooled and separated from inorganic salts through filtration, acetone was distilled away therefrom. The residue was purified through a column-chromatography [silica gel, developed with ethyl acetate/n-hexane=1/1(V/V)] to give 1.07 g of the title compound (yield 60%), which was recrystallized from a mixed solvent of benzene-n-hexane to afford a crystal of melting point 133°–134° C.

SYNTHESIS EXAMPLE 2

N-3-methoxyphenyl-2-[4-(4-cyanophenoxy)-phenoxy]-propionamide (Compound No. 9)

Into 10 ml of diethylether containing 0.81 g of m-anisidine, diethylether solution of 1.0 g of 4-(4-cyanophenoxy)$\alpha$-phenoxy-propionic acid chloride was added dropwise at room temperature.

After the reaction mixture was stirred for 6 hours at room temperature, water was added thereinto and ether layer thereof was separated. After the ether layer was washed with dilute hydrochloric acid and water in this order, it was dried over anhydrous magnesium sulfate. After a filtration of this desiccant, ether was distilled away therefrom. The obtained residue was purified through a column-chromatography(silica gel, developed with benzene) to give 0.98 g of the title compound (yield 77%), of which melting point was 118°–119.5° C.

SYNTHESIS EXAMPLE 3

N-(6-methyl-2-pyridyl)-2-[4-(4-cyanophenoxy)-phenoxy]-propionamide (Compound No. 23)

To 100 ml of dichloromethane solution containing 1.99 g of 2-[4-(4-cyanophenoxy)-phenoxy]-propionic acid, which was cooled with ice water, was added slowly 1,46 g of dicyclohexylcarbodiimide with stirring. After this mixture was stirred for 15 minutes, 0.76 g of 2-amino-6-methylpyridine was added thereinto with stirring. A temperature of reacting mixture was returned to room temperature with stirring. A precipitated solid was removed through filtration, and then the obtained solution was poured into 200 ml of chilled water. An organic layer was separated therefrom, and it was washed with dilute hydrochloric acid, saturated aqueous solution of sodium bicarbonate and saturated aqueous solution of sodium chloride in this order, from which the solvent was distilled away after drying. The residue was purified through a column-chromatography [silica gel, developed with benzene/ethyl acetate=10/1(V/V)] to give 1.53 g of the title compound having melting point of 109°–111° C.

FORMULATION EXAMPLE 1

(Water dispersible powder)

A water dispersible powder was prepared by mixing and pulverizing 20 parts (the term "parts" means parts by weight, which is the same hereinafter) of Compound No. 1 of this invention, 15 parts of diatomaceous earth, 60 parts of clay, 3 parts of sodium ligninsulfate and 2 parts of dodecylbenzenesulfonate.

FORMULATION EXAMPLE 2

(Emulsifiable concentrate)

An emulsifiable concentrate was prepared by mixing 20 parts of Compound No. 8 of this invention, 72 parts of xylene, 3 parts of polyoxyethylenealkylether, 2 parts of polyoxyethylenealkylallylether and 3 parts of calcium alkylbenzenesulfonate each other to give a homogeneous solution.

FORMULATION EXAMPLE 3

(Granules)

After 5 parts of Compound No. 13 of this invention, 22 parts of bentonite, 42.5 parts of talc, 2.8 parts of clay, 2 parts of sodium ligninsulfonate and 0.5 part of sodium dodecylbenzenesulfonate were admixed uniformly and then added with water, the resulted mixture was extruded and formed into a granular form through a granulator, which were thereafter dried and separated through a sieve to give granules.

Next, herbicidal activities of the compounds of this invention are explained by the following test examples.

TEXT EXAMPLE 1

(Activity test against barnyard grass)

Into Wagner pots having a dimension "one five thousandth are" were charged paddy field soils respectively, which were then tilled, and thereafter 50 barnyard grass seeds were sown thereon. At the time of germination of barnyard grass seeds and the time of arrival to 2-leaf stage with keeping water depth of the flooded pots to be 3 cm respectively, desired amounts of the emulsifiable concentrate, which were previously prepared from the compounds of this invention according to the Formulation Example 2, was diluted with water and then added uniformly on the water surface of each pot for treatment thereof.

On 15th day after the treatment, the herbicidal activities were examined. The results were shown in Table 1. The herbicidal activities were evaluated by the following standard.

| Estimation Index | Herbicidal activities |
| --- | --- |
| 5 | Killed |
| 4 | 80–99% Prevention |
| 3 | 60–79% Prevention |
| 2 | 40–59% Prevention |
| 1 | 20–39% Prevention |
| 0 | No Prevention |

TABLE 1

| Compound No. | Barnyard grass in germination stage Effective dose kg/ha | |
| --- | --- | --- |
| | 1 | 0.25 |
| 1 | 5 | 5 |
| 2 | 5 | 5 |
| 3 | 5 | 5 |
| 4 | 5 | 5 |
| 5 | 5 | 5 |
| 6 | 5 | 5 |
| 7 | 5 | 5 |
| 8 | 5 | 5 |
| 9 | 5 | 5 |
| 10 | 5 | 5 |

TABLE 1-continued

| Compound No. | Barnyard grass in germination stage Effective dose kg/ha | |
| --- | --- | --- |
| | 1 | 0.25 |
| 11 | 5 | 5 |
| 12 | 5 | 5 |
| 13 | 5 | 5 |
| 14 | 5 | 5 |
| 15 | 5 | 5 |
| 16 | 5 | 5 |
| 17 | 5 | 5 |
| 18 | 5 | 5 |
| 19 | 5 | 5 |
| 20 | 5 | 3 |
| 21 | 5 | 2 |
| 22 | 5 | 5 |
| 23 | 5 | 5 |
| Not treated | 0 | 0 |
| 24 | 5 | 2 |
| 25 | 5 | 5 |
| 26 | 5 | 2 |
| 27 | 5 | 5 |
| 28 | 5 | 5 |
| 29 | 5 | 5 |
| 30 | 5 | 5 |
| 31 | 5 | 2 |
| 32 | 5 | 5 |
| 33 | 5 | 4 |
| 34 | 5 | 5 |
| 35 | 5 | 4 |
| 36 | 5 | 3 |
| 37 | 5 | 3 |
| 38 | 5 | 4 |
| 39 | 5 | 4 |
| 40 | 5 | 2 |
| 41 | 5 | 5 |
| 42 | 5 | 5 |
| 43 | 5 | 5 |
| 44 | 5 | 5 |
| 45 | 5 | 5 |
| 46 | 5 | 5 |
| Reference compound 1* | 0 | 0 |
| Reference compound 2** | 0 | 0 |

*Reference compound 1 (Compound described in Japanese unexamined publication Sho 53-9740

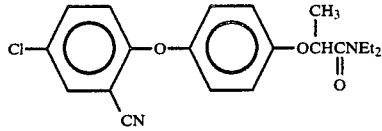

**Reference compound 2

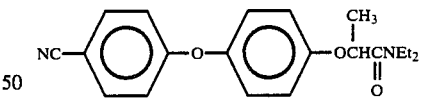

TEST EXAMPLE 2

(Prevention test of barnyard grass under submerged condition of rice direct seeding)

After paddy field soils were filled respectively into Wagner pots having a dimension "one five thousandth are" and then tilled, 20 rice plant seeds (variety: Nihonbare) and 50 barnyard grass seeds were sown thereon. At the time of germinations of the rice plant seeds and the barnyard grass seeds, desired amounts of the emulsifiable concentrate, which were previously prepared from the compound of this invention according to the Formulation Example 2, was diluted with water and then added uniformly on the water surface of each flooded pot, in which water depth was kept to be 3 cm respectively, for treatment thereof.

On 14th day after the treatment, herbicidal activities and phytotoxicities were examined to obtain the results of Table 2.

TABLE 2

| Compound No. | Division of Rice plant or Barnyard grass | Effective dose kg/ha | |
|---|---|---|---|
| | | 1 | 0.25 |
| 2 | R.P. | 82 | 100 |
| | B.G. | 0 | 0 |
| 3 | R.P. | 90 | 100 |
| | B.G. | 0 | 0 |
| 4 | R.P. | 88 | 100 |
| | B.G. | 0 | 0 |
| 5 | R.P. | 87 | 100 |
| | B.G. | 0 | 0 |
| 6 | R.P. | 85 | 100 |
| | B.G. | 0 | 0 |
| 8 | R.P. | 86 | 100 |
| | B.G. | 0 | 0 |
| 11 | R.P. | 92 | 100 |
| | B.G. | 0 | 0 |
| 12 | R.P. | 100 | 100 |
| | B.G. | 0 | 0 |
| 13 | R.P. | 100 | 100 |
| | B.G. | 0 | 0 |
| 14 | R.P. | 100 | 100 |
| | B.G. | 0 | 0 |
| 16 | R.P. | 81 | 100 |
| | B.G. | 0 | 0 |
| 17 | R.P. | 83 | 100 |
| | B.G. | 0 | 0 |
| 18 | R.P. | 95 | 100 |
| | B.G. | 0 | 0 |
| 22 | R.P. | 82 | 100 |
| | B.G. | 0 | 0 |
| 23 | R.P. | 90 | 100 |
| | B.G. | 0 | 0 |
| 28 | R.P. | 100 | 100 |
| | B.G. | 0 | 0 |
| 29 | R.P. | 100 | 100 |
| | B.G. | 0 | 0 |
| 41 | R.P. | 100 | 100 |
| | B.G. | 0 | 0 |
| 42 | R.P. | 100 | 100 |
| | B.G. | 0 | 0 |
| 43 | R.P. | 100 | 100 |
| | B.G. | 0 | 0 |
| 44 | R.P. | 97 | 100 |
| | B.G. | 0 | 0 |
| 45 | R.P. | 84 | 100 |
| | B.G. | 0 | 0 |
| 46 | R.P. | 100 | 100 |
| | B.G. | 0 | 0 |
| Not treated | R.P. | 100 | 100 |
| | B.G. | 100 | 100 |

(Numerical value represents ratio of living body weight to not-treated one)
Rice plant is abbreviated to as R.P., and Barnyard grass is abbreviated to as B.G.

What is claimed is:

1. A 2-[4-(4-cyanophenoxy)-phenoxy]-alkanoic acid amide of the formula (I)

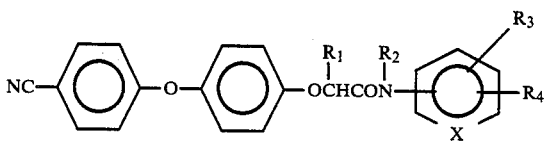

wherein
R$_1$ is hydrogen or methyl,
R$_2$ is selected from the group consisting of hydrogen and lower alkyl,
R$_3$ is selected from the group consisting hydrogen, halogen, lower alkyl, lower alkoxy, cyano, nitro, trifluoromethyl, lower alkylaminocarbonyl and lower alkanesulfonyloxy,
R$_4$ is selected from the group consisting of hydrogen, halogen and lower alkyl, and
X is selected from the group consisting of methine and nitrogen.

2. The 2-[4-(4-cyanophenoxy)-phenoxy]-alkanoic acid amide of claim 1, wherein R$_1$ is methyl.

3. The 2-[4-(4-cyanophenoxy)-phenoxy]-alkanoic acid amide of claim 1, wherein R$_2$ is hydrogen.

4. The 2-[4-(4-cyanophenoxy)-phenoxy]-alkanoic acid amide of claim 1, wherein R$_3$ is selected from the group consisting of hydrogen, halogen, lower alkyl and lower alkoxy, and R$_4$ is selected from the group consisting of is hydrogen and lower alkyl.

5. The 2-[4-(4-cyanophenoxy)-phenoxy]-alkanoic acid amide of claim 1, wherein
R$_1$ is methyl,
R$_2$ is hydrogen,
R$_3$ is selected from the group consisting of hydrogen, halogen, lower alkyl and lower alkoxy,
R$_4$ is selected from the group consisting of hydrogen and lower alkyl.

6. The compound of claim 1 being N-(2-fluorophenyl)-2-[4-(4-cyanophenoxy)-phenoxy]propionamide.

7. The compound of claim 1 being N-(3-fluorophenyl)-2-[4-(4-cyanophenoxy)-phenoxy]propionamide.

8. The compound of claim 1 being N-(4-fluorophenyl)-2-[4-(4-cyanophenoxy)-phenoxy]propionamide.

9. The compound of claim 1 being N-(2-chlorophenyl)-2-[4-(4-cyanophenoxy)-phenoxy]propionamide.

10. The compound of claim 1 being N-(2-methoxyphenyl)-2-[4-(4-cyanophenoxy)-phenoxy]propionamide.

11. The compound of claim 1 being N-(3-methoxyphenyl)-2-[4-(4-cyanophenoxy)-phenoxy]propionamide.

12. The compound of claim 1 being N-(2-methylphenyl)-2-[4-(4-cyanophenoxy)-phenoxy]propionamide.

13. The compound of claim 1 being N-(3-methylphenyl)-2-[4-(4-cyanophenoxy)-phenoxy]propionamide.

14. The compound of claim 1 being N-(4-methylphenyl)-2-[4-(4-cyanophenoxy)-phenoxy]propionamide.

15. The compound of claim 1 being N-(2-pyridyl)-2-[4-(4-cyanophenoxy)-phenoxy]-propionamide.

16. The compound of claim 1 being N-(4-methyl-2-pyridyl)-2-[4-(4-cyanophenoxy)-phenoxy]-propionamide.

17. The compound of claim 1 being N-(6-methyl-2-pyridyl)-2-[4-(4-cyanophenoxy)-phenoxy]-propionamide.

18. The compound of claim 1 being N-(5-chloro-2-pyridyl)-2-[4-(4-cyanophenoxy)-phenoxy]-propionamide.

19. The compound of claim 1 being N-(3-isopropoxyphenyl)-2-[4-(4-cyanophenoxy)-phenoxy]propionamide.

20. The compound of claim 1 being N-(6-methoxy-2-pyridyl)-2-[4-(4-cyanophenoxy)-phenoxy]-propionamide.

21. The compound of claim 1 being N-(4,6-dimethyl-2-pyridyl)-2-[4-(4-cyanophenoxy)-phenoxy]propionamide.

22. A herbicide comprising:
a herbicially-effective amount of a 2-[4-(4-cyanophenoxy)-phenoxy]-alkanoic acid amide of the formula (I)

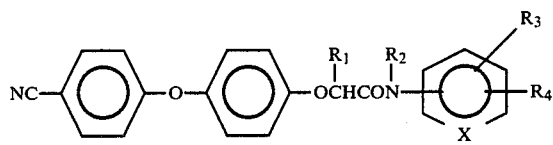

wherein
$R_1$ is selected from the group consisting of hydrogen and methyl,
$R_2$ is selected from the group consisting of hydrogen and lower alkyl,
$R_3$ is selected from the group consisting of hydrogen, halogen, lower alkyl, lower alkoxy, cyano, nitro, trifluoromethyl, lower alkylaminocarbonyl and lower alkanesulfonyloxy,
$R_4$ is selected from the group consisting of hydrogen, halogen and lower alkyl, and
X is selected from the group consisting of methine and nitrogen; and
a diluent.

23. The herbicide of claim 22 wherein the diluent is a solvent or a surface active agent.

24. The herbicide of claim 22 formulated as an emulsifiable concentrate.

25. The herbicide of claim 22 formulated as a water dispersible powder.

26. The herbicide of claim 22 formulated in the form of a dust.

27. The herbicide of claim 22 formulated in the form of granules.

* * * * *